United States Patent
Maier et al.

(10) Patent No.: US 6,989,462 B2
(45) Date of Patent: Jan. 24, 2006

(54) SYNTHESIS OF 2-CHLOROMETHYL-6-METHYLBENZOIC ESTER

(75) Inventors: Claus-Jürgen Maier, Hemsbach (DE); Tobias Metzenthin, Hofheim (DE); Joachim Graeser, Kelsterbach (DE); Richard Bicker, Liederbach (DE); Javier Manero, Liederbach (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 0 days.

(21) Appl. No.: 10/803,578

(22) Filed: Mar. 18, 2004

(65) Prior Publication Data

US 2004/0192956 A1    Sep. 30, 2004

Related U.S. Application Data

(60) Provisional application No. 60/491,651, filed on Jul. 31, 2003.

(30) Foreign Application Priority Data

Mar. 25, 2003   (DE)   ................. 103 13 228

(51) Int. Cl.
   C07C 69/017   (2006.01)
   C07C 69/00    (2006.01)
   C07C 63/04    (2006.01)

(52) U.S. Cl. .................... 560/103; 560/8; 560/106; 560/107; 560/108; 560/110; 560/111; 560/112; 560/113; 562/405; 562/493

(58) Field of Classification Search .............. 560/8, 560/103, 106, 107, 108, 110, 111, 112, 113; 562/405, 493
   See application file for complete search history.

(56) References Cited

U.S. PATENT DOCUMENTS 4,585,788 A * 4/1986 Helsley et al. .............. 514/450

FOREIGN PATENT DOCUMENTS

| WO | WO 00/64876 | 11/2000 |
| WO | WO 00/64888 | 11/2000 |
| WO | WO 03/020269 | 3/2003 |

OTHER PUBLICATIONS

Tilstam Ulf et al., Trichloroisocyanuric Acid: A Safe and Efficient Oxidant, Org Process Research & Development, vol. 6, 2002, pp 384-393.

* cited by examiner

*Primary Examiner*—Elvis O. Price
(74) *Attorney, Agent, or Firm*—Irving Newman

(57) ABSTRACT

A process is described for preparing compounds of formula (I)

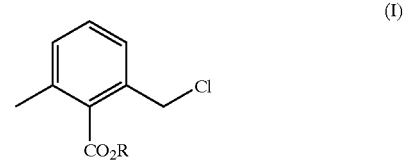

where R is H, optionally halogen-substituted alkyl, cycloalkyl, aryl, alkyl-aryl or heteroaryl, and, in alkyl and cycloalkyl, one or more $CH_2$ groups may be replaced by —O—. The compounds of the formula (I) are valuable intermediates in the synthesis of PPAR agonists.

7 Claims, No Drawings

SYNTHESIS OF 2-CHLOROMETHYL-6-METHYLBENZOIC ESTER

CROSS-REFERENCE TO RELATED APPLICATIONS

This application claims the benefit of U.S. Provisional Application No. 60/491,651, filed Jul. 31, 2003. This application also claims priority from German Application No. 10313228.7-44, filed on Mar. 25, 2003.

FIELD OF THE INVENTION

This invention provides a novel, improved method for synthesizing certain halogenated methylbenzoic esters.

BACKGROUND OF THE INVENTION

2-Haloalkylbenzoic acid derivatives are used as building blocks for the synthesis of active pharmaceutical ingredients. For various reasons, it is desirable for the use to have storage-stable compounds which can additionally be prepared and purified in a simple manner. These reasons include, for example, the ensuring of a constant quality, the avoidance of frequent checks on the materials to record the product quality, the avoidance of the necessity of cold storage and/or cold transport, easy transfer to production plants and also simple cleaning of used vessels.

2-Bromomethyl-6-methylbenzoic esters (A1 and A2) are known, for example, from WO 00/64888 (R=iBu (A1)) and WO 00/64876 (R=Me (A2)). These compounds are not storage-stable at room temperature, since they cyclize spontaneously to the lactone (B) and in the process, as is well known, release mutagenic alkyl bromides as a by-product.

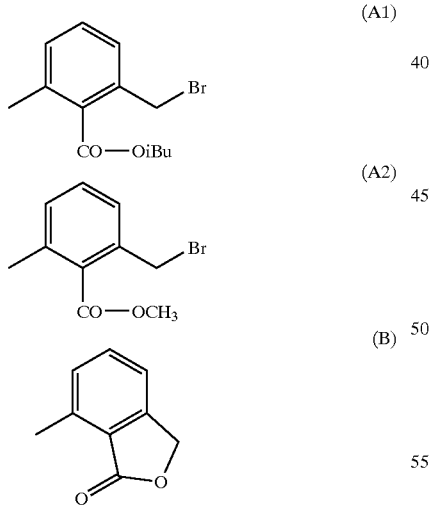

The use of these thermally labile substances on an industrial scale is therefore associated with occupational hygiene risks, difficulties and additional costs.

DETAILED DESCRIPTION

Among other uses, the 2-bromomethyl-6-methylbenzoic esters are of interest as starting materials for the preparation of PPAR agonists, as described, for example, in WO 00/64888, WO 00/64876 and WO 03/020269. Particular mention should be made here of the compounds of the formula (C):

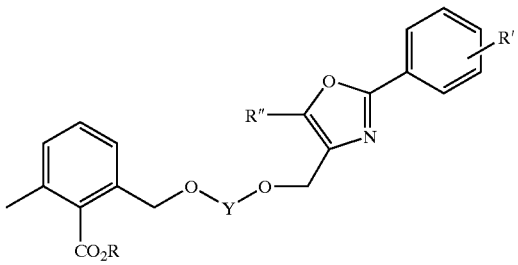

where
  R is selected from the group consisting of H, $C_2$–$C_{12}$-alkyl, $C_3$–$C_8$-cycloalkyl, $C_6$–$C_{12}$-aryl, $C_1$–$C_4$-alkyl-$C_6$–$C_{12}$-aryl and $C_5$–$C_{10}$-heteroaryl, wherein, in the alkyl and cycloalkyl groups, one or more $CH_2$ groups may be replaced by —O— and the alkyl, cycloalkyl and aryl groups may be optionally substituted with halogen,
  Y is —$(CH_2)_3$—, 1,3-phenylene, or 1,3-cyclohexanediyl;
  R' is selected from H, F, Br, $CF_3$, $(C_1$–$C_6)$-alkyl, O—$(C_1$–$C_6)$-alkyl, and phenyl; and
  R" is selected from H, $(C_1$–$C_6)$-alkyl, $(C_1$–$C_3)$-alkylphenyl, $(C_5$–$C_6)$-cycloalkyl, phenyl, and $CF_3$.

Preference is given to the compounds of formula (C) in which the phenyl ring is substituted by R' in the m- or p-position.

It is thus an object of the invention to find more stable compounds than (A1) and (A2) which do not have the above-outlined disadvantages. In addition, the target compounds, which can occur in a purity which is not yet sufficient, particularly when they are prepared from a crude product, should, in contrast to the compounds of the formulae (A1) and (A2), be purifiable.

This is achieved by the compounds of the formula (I) described below.

The present invention provides the compounds of formula (I)

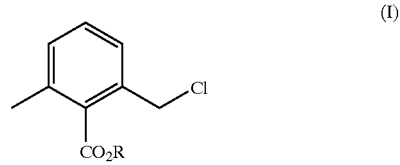

wherein:
  R is selected from the group consisting of H, $C_1$–$C_{12}$-alkyl, $C_3$–$C_8$-cycloalkyl, $C_6$–$C_{12}$-aryl, $C_1$–$C_4$-alkyl-$C_6$–$C_{12}$-aryl and $C_5$–$C_{10}$-heteroaryl, wherein, in the alkyl and cycloalkyl groups, one or more $CH_2$ groups may be replaced by —O—, and each of the alkyl, cycloalkyl and aryl groups may be independently substituted with halogen.

Preference is given to the compounds of formula (I) in which
R is selected from $C_1$–$C_8$ alkyl, $C_3$–$C_6$-cycloalkyl and $C_1$–$C_4$-alkyl-$C_6$–$C_{12}$-aryl, each of which may optionally be substituted by halogen and in which one or two $CH_2$ groups may be replaced by —O—.

Particular preference is given to the compounds of formula (I) in which
R is $C_1$–$C_6$ alkyl or $C_1$–$C_4$-alkyl-$C_6$–$C_{12}$-aryl, each of which may optionally be independently substituted by halogen and in which one $CH_2$ group may be replaced by —O—.

Very particular preference is given to compounds of formula (I) in which
R is methyl, ethyl, propyl, i-propyl, t-butyl, phenyl, 2-methoxyethyl or benzyl.

Alkyl may be branched or unbranched. Halogen is Cl, Br, I, preferably Cl. In this context, heteroaryl refers to 5- to 10 membered aromatic rings which contain from one to four identical or different heteroatoms selected from the group consisting of N, O, and, S, for example, pyrrole, imidazole, pyrazole, pyridine, pyrazine, pyrimidine, pyridazine, furan, thiophene, oxazole, isoxazole, thiazole, isothiazole, triazole, tetrazole, triazine, and tetrazine; preference is given to: pyrrole, imidazole, oxazole, thiazole and pyridine.

The present invention also provides a process for preparing the compounds of formula (I)

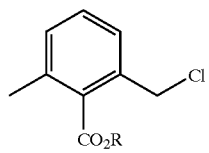

wherein:
R is selected from the group consisting of H, $C_1$–$C_{12}$-alkyl, $C_3$–$C_8$-cycloalkyl, $C_6$–$C_{12}$-aryl, $C_1$–$C_4$-alkyl-$C_6$–$C_{12}$-aryl and $C_5$–$C_{10}$-heteroaryl, and, wherein, in the alkyl and cycloalkyl groups, one or more $CH_2$ groups may be replaced by —O—, and the alkyl, cycloalkyl and aryl groups may be independently substituted by halogen, which comprises
reacting dimethylbenzoic esters of formula (II)

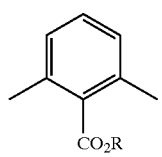

where R is as defined above with a chlorinating reagent, for example sulfuryl chloride, N-chlorosuccinimide (NCS), 1,3-dichloro-5,5-dimethylhydantoin (NDDH) or trichloroisocyanuric acid [Org Process Research & Development 2002,6,384-393], in an inert solvent, for example, $CCl_4$, chlorobenzene, or without solvents, at a temperature above 40° C., and subsequently optionally purifying.

Preferably, the reaction is carried out at 60–90° C., although chlorination on the aromatic ring is observed at lower temperatures. The purification is preferably accomplished by distillation or by a silica gel filtration.

The chlorine compounds of formula (I) are only obtainable very inefficiently, if at all, by a ring-opening chlorination of the lactones (B), since the lactone structure is very stable. In addition, surprisingly, the 2-chloromethylbenzoic acid derivatives can be distilled, can be isolated by this method in excellent chemical purity and do not react spontaneously in the course of storage to give the lactones.

A conversion of the chlorine compounds of formula (I) to more reactive bromine or iodine compounds may likewise be advantageous, in order to increase the reactivity of this molecular building block in the further synthesis (for example to give PPAR agonists (C)). However, these compounds then have the "technical" disadvantages mentioned in the introduction. The conversion of the chlorine into the bromine or iodine compound is effected with alkali metal halides in inert solvents, preferably with sodium bromide or iodide in acetone under reflux. Alternatively, the transhalogenation and the further synthesis can also be carried out as a one-pot method with catalytical or stoichiometric amounts of alkyl halide, based on the chlorine compound used.

The present invention further provides a process for preparing the compounds of formula (C)

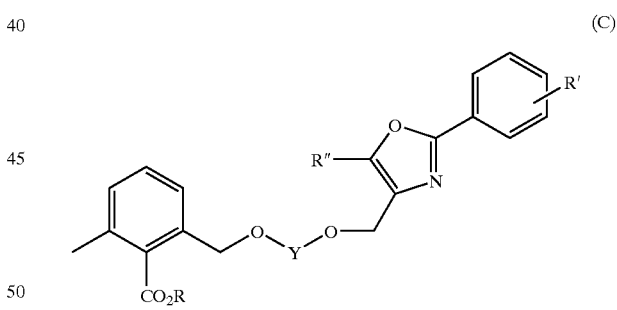

in which
R is selected from H, $C_1$–$C_{12}$-alkyl, $C_3$–$C_8$-cycloalkyl, $C_6$–$C_{12}$-aryl, $C_1$–$C_4$-alkyl-$C_6$–$C_{12}$-aryl and $C_5$–$C_{10}$-heteroaryl and wherein, in the alkyl and cycloalkyl groups, one or more $CH_2$ groups may be replaced by —O— and the alkyl, cycloakyl and aryl groups may independently be substituted by halogen, Y is —$(CH_2)_3$—, 1,3-phenylene, or 1,3-cyclohexanediyl, R' is selected from H, F, Br, $CF_3$, ($C_1$–$C_6$)-alkyl, O—($C_1$–$C_6$)-alkyl, and phenyl;

R" is selected from H, ($C_1$–$C_6$)-alkyl, ($C_1$–$C_3$)-alkylphenyl, ($C_5$–$C_6$)-cycloalkyl, phenyl, and $CF_3$;

which comprises reacting a compound of formula (C1)

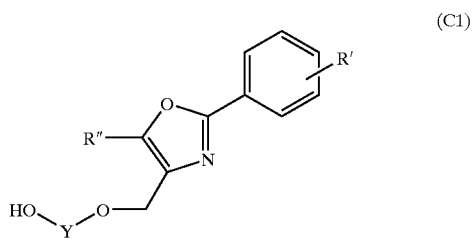

wherein Y, R' and R" are each as defined above with a compound of formula (I)

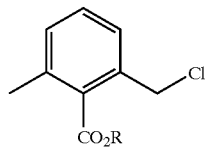

where R is as defined above in toluene, NMP or another aprotic solvent, in the presence of a suitable base, preferably with potassium tert-butoxide, at a temperature from −78 to +50° C., preferably at from about −30 to +20° C., and subsequently working up extractively and optionally crystallizing the end product.

The compounds of formula (I) are notable for high stability compared to the corresponding bromine compounds. When the stability of methyl 2-bromomethyl-6-methylbenzoate is compared to that of the analogous chlorine compound, the following result is obtained: methyl 2-chloromethyl-6-methylbenzoate can be distilled without decomposition at 66–77° C./0.1 mbar, and only a bottom temperature of above 120° C. leads to significant lactone formation. At room temperature, it can be stored stably over several months. The storage stability of methyl 2-bromomethyl-6-methylbenzoate differs distinctly from this. At room temperature, the content of the bromine compound reduces sharply within a few days; within one week, from 92.6 to 81.0%; within 2 weeks, to 67.8% and within 2 months, to 7.8%. At the same time, the lactone content rises from 1.9% to 13.9% after 1 week and 89.5% in 2 months.

The following non-limiting examples are illustrative:

EXAMPLE 1

Synthesis of methyl 2-chloromethyl-6-methylbenzoate 11.9 g of methyl 2,6-dimethylbenzoate are initially charged in 50 ml of chlorobenzene admixed at room temperature with 8.2 g of sulfuryl chloride and 40 mg of AIBN. The mixture is stirred at 60–90° C. for 2 h. Afterwards, the mixture is admixed with 80 ml of saturated NaHCO₃ solution. After the phase separation, the organic phase is washed with 100 ml of 10% Na₂SO₃ solution, the organic phase is dried over magnesium sulfate and the chlorobenzene is distilled off in vacuo. 15.5 g of colorless liquid are obtained. The product is distilled under high vacuum (0.1 mbar, 66–77° C.). Yield: 10.2 g (71% of theory; 95.2 area %).

EXAMPLE 2

Synthesis of isopropyl 2-chloromethyl-6-methylbenzoate 19.2 g of isopropyl 2,6-dimethylbenzoate are initially charged in 100 ml of carbon tetrachloride admixed at room temperature with 13.3 g of N-chlorosuccinimide and 200 mg of AIBN. The mixture is heated to reflux for 3 h. After the mixture has been cooled, it is filtered with suction, and the succinimide is washed with 20 ml of carbon tetrachloride. The filtrates are combined, and carbon tetrachloride is distilled off in vacuo. 21.8 g of colorless liquid are obtained. The product is distilled under high vacuum (0.05 mbar, 94–97° C.). Yield: 13.9 g (61% of theory; 93.6 area %).

EXAMPLE 3

Synthesis of 2-methoxyethyl 2-chloromethyl-6-methylbenzoate 10.4 g of 2-methoxyethyl 2,6-dimethylbenzoate are admixed at room temperature with 5.4 g of sulfuryl chloride and 40 mg of AIBN. The mixture is stirred at 60–90° C. for 1–2 h. Afterwards, the mixture is admixed with 20 ml of water, the phases are separated and the organic phase is dried over magnesium sulfate. The product is distilled under high vacuum (0.02 mbar, 95–103° C.). Yield: 6.4 g (66% of theory; 91.8 area %).

EXAMPLE 4

Synthesis of benzyl 2-chloromethyl-6-methylbenzoate 12.0 g of benzyl 2,6-dimethylbenzoate are initially charged into 50 ml of carbon tetrachloride admixed at room temperature with 5.4 g of sulfuryl chloride and 40 mg of AIBN. The mixture is stirred at reflux for 4–5 h. Afterwards, it is admixed with 40 ml of saturated NaHCO₃ solution. After the phase separation, the organic phase is washed with 50 ml of 10% sodium sulfite solution, and the organic phase is then dried over magnesium sulfate. The product-containing solution is filtered trough silica gel and washed again with 20 ml of carbon tetrachloride. After distilling off the solvent in vacuo, the product obtained is a bright yellow oil. Yield: 8.0 g (73% of theory; 88.4 area %).

EXAMPLE 5

2-Methyl-6-[3-(2-phenyloxazol-4-ylmethoxy)propoxymethyl]benzoic acid 4.8 g of methyl 2-chloromethyl-6-methylbenzoate are dissolved at room temperature in 250 ml of acetone and admixed with 35 g of sodium iodide. The mixture is heated to reflux for 6 h. Subsequently, the solvent is removed at 0° C. in vacuo. The residue is analyzed by means of LC-MS (87.7 area % of methyl 2-iodomethyl-6-methylbenzoate) and dissolved in 20 ml of toluene. The solution is added dropwise at −20° C. within 10 min to a mixture of 5.0 g of 3-(2-phenyloxazol-4-ylmethoxy)propan-1-ol, 4.8 g of potassium tert-butoxide and 30 ml of toluene. Afterwards, the mixture is stirred at −20° C. for 6 h and diluted with 100 ml of water, and the aqueous phase is removed. The organic phase is admixed with 40 ml of NMP and 10 ml of 32% sodium hydroxide solution and heated to reflux for 8 h on a water separator. Subsequently, the mixture is admixed with 100 ml of water and extracted twice with 25 ml of MTB ether each time. The aqueous phase is acidified with 5 ml of acetic acid and extracted twice with 50 ml of ethyl acetate each time. After the phases have been separated, the organic phase is dried over magnesium sulfate and the solvent is removed in vacuo. After the crystallization from diisopropyl ether, 4.2 g of 2-methyl-6-[3-(2-phenyloxazol-4-ylmethoxy) propoxymethyl]benzoic acid (50% of theory, 99.2 HPLC area %) are obtained.

What is claimed is:

1. A compound of formula (I)

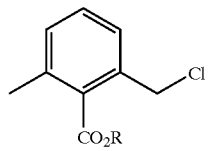

(I)

wherein:
R is selected from the group consisting of H, $C_1$–$C_{12}$-alkyl, $C_3$–$C_8$-cycloalkyl, $C_6$–$C_{12}$-aryl, and $C_1$–$C_4$-alkyl-$C_6$–$C_{12}$-aryl, wherein, in the alkyl and cycloalkyl groups, one or more $CH_2$ groups may be replaced by —O—, and each of the alkyl, cycloalkyl and aryl groups may be independently substituted with halogen.

2. A compound of formula (I) as claimed in claim 1 in which
R is selected from the group consisting of $C_1$–$C_8$ alkyl, $C_3$–$C_6$-cycloalkyl and $C_1$–$C_4$-alkyl-$C_6$–$C_{12}$-aryl, each of which may optionally be independently substituted with halogen and in which one or two $CH_2$ groups may be replaced by —O—.

3. A compound of formula (I) as claimed in claim 1 in which
R is $C_1$–$C_6$ alkyl or $C_1$–$C_4$-alkyl-$C_6$–$C_{12}$-aryl, each of which may optionally be independently substituted with halogen and in which one $CH_2$ group may be replaced by —O—.

4. A compound of formula (I) as claimed in claim 1 in which
R is methyl, ethyl, propyl, i-propyl, t-butyl, phenyl, 2-methoxyethyl or benzyl.

5. A process for preparing a compound of formula (I) as claimed in claim 1, which comprises
reacting a dimethylbenzoic ester of formula (II)

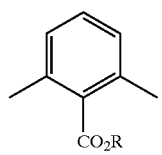

(II)

where R is as defined in claim 1 above
with a chlorinating reagent, optionally in an inert solvent, at a temperature above 40° C. and subsequently optionally purifying.

6. A process for preparing a compound of formula (C)

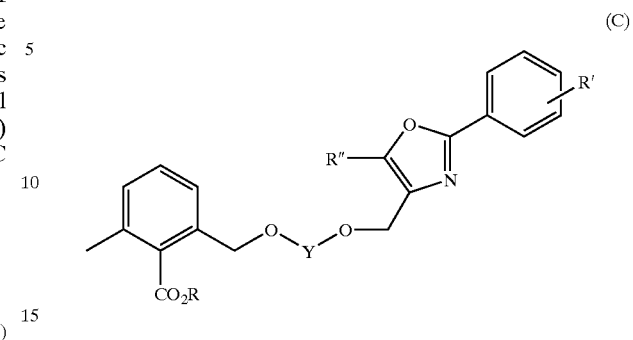

(C)

in which
R is selected from the group consisting of H, $C_1$–$C_{12}$-alkyl, $C_3$–$C_8$-cycloalkyl, $C_6$–$C_{12}$-aryl, and $C_1$–$C_4$-alkyl-$C_6$–$C_{12}$-aryl and, wherein, in the alkyl and cycloalkyl groups, one or more $CH_2$ groups may be replaced by —O— and the alkyl, cycloakyl and aryl groups may be independently substituted by halogen,
Y is —$(CH_2)_3$—, 1,3-phenylene, or 1,3-cyclohexanediyl,
R' is selected from H, F, Br, $CF_3$, ($C_1$–$C_6$)-alkyl, O—($C_1$–$C_6$)-alkyl, and phenyl;
R" is selected from H, ($C_1$–$C_6$)-alkyl, ($C_1$–$C_3$)-alkylphenyl, ($C_5$–$C_6$)-cycloalkyl, phenyl, and $CF_3$;
which comprises reacting a compound of the formula (C1)

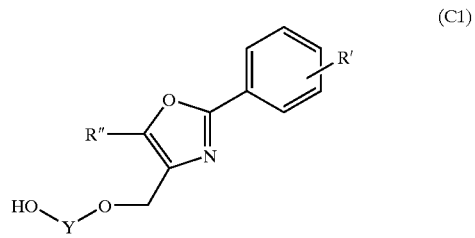

(C1)

where Y, R' and R" are each as defined above in this claim with a compound of the formula (I)

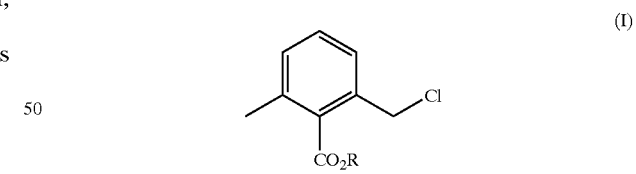

(I)

where R is as defined above in this claim
in toluene, N-methyl-2-pyrrolidinon (NMP) or other aprotic solvents, in the presence of potassium tert-butoxide, at a temperature in the range of −78 to +50° C., and subsequently working up extractively and optionally crystallizing the end product.

7. The process for preparing the compounds of formula (C) as claimed in claim 6, wherein the phenyl ring is substituted by R' in the m- or p-position.

* * * * *